United States Patent
O'Shaughnessy et al.

(10) Patent No.: US 11,819,199 B2
(45) Date of Patent: Nov. 21, 2023

(54) RAMPED BIOPSY NEEDLE DEVICE

(71) Applicant: BOSTON SCIENTIFIC SCIMED, INC., Maple Grove, MN (US)

(72) Inventors: Seamus O'Shaughnessy, Chelmsford, MA (US); Colby Harris, Weston, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 357 days.

(21) Appl. No.: 16/285,673

(22) Filed: Feb. 26, 2019

(65) Prior Publication Data

US 2019/0328371 A1  Oct. 31, 2019

Related U.S. Application Data

(60) Provisional application No. 62/664,674, filed on Apr. 30, 2018.

(51) Int. Cl.
*A61B 10/04* (2006.01)
*A61B 10/02* (2006.01)

(52) U.S. Cl.
CPC .......... *A61B 10/0266* (2013.01); *A61B 10/04* (2013.01); *A61B 2010/0208* (2013.01); *A61B 2010/0225* (2013.01); *A61B 2010/045* (2013.01)

(58) Field of Classification Search
CPC ......... A61B 10/0233–0283; A61B 2010/0258; A61B 2010/0225; A61B 10/02;

(Continued)

(56) References Cited

U.S. PATENT DOCUMENTS 5,350,393 A  9/1994  Yoon
5,908,381 A  6/1999  Aznoian et al.
(Continued)

FOREIGN PATENT DOCUMENTS

CN  101932288  12/2010
CN  104203327  12/2014
(Continued)

OTHER PUBLICATIONS

Machine translation of CN 106725249 retrieved from worldwide.espacenet.com on Mar. 24, 2021 (Year: 2017).*

*Primary Examiner* — Daniel L Cerioni
(74) *Attorney, Agent, or Firm* — Fay Kaplun & Marcin, LLP

(57) ABSTRACT

A biopsy needle system includes a needle extending from a tissue piercing distal end to a proximal end. The needle defines a lumen extending from the distal end at least a portion of a length thereof and houses a target tissue. The system also includes an elongated member defining a channel therethrough open at a proximal end. The channel is sized and shaped to permit passage of the needle therethrough. Further, the system includes an end cap coupled to the distal end of the elongate member. The end cap includes a hole extending through a lateral wall thereof. The hole is sized and shaped to permit passage of the needle therethrough. The end cap further includes a ramp extending from the channel to the hole to guide the needle through the hole. The ramp is angled with respect to a longitudinal axis of the elongated member.

9 Claims, 4 Drawing Sheets

(58) Field of Classification Search
CPC ............... A61B 10/0291; A61B 10/04; A61B 2010/0208; A61B 2010/045; A61B 10/0041; A61B 17/0482; A61B 2017/3405–3411; A61B 17/3478; A61B 2017/3413; A61B 8/12; A61B 17/32053; A61B 17/320016; A61B 17/06; A61B 2017/06071–06104; A61B 10/0266
See application file for complete search history.

(56) References Cited

U.S. PATENT DOCUMENTS

| | | | | |
|---|---|---|---|---|
| 6,203,524 B1* | 3/2001 | Burney | ............... | A61B 10/0233 128/898 |
| 2005/0124914 A1* | 6/2005 | Dicarlo | ............... | A61B 10/0275 600/567 |
| 2005/0283178 A1* | 12/2005 | Flagle | ............... | A61M 25/10 606/191 |
| 2008/0262515 A1* | 10/2008 | Makower | ............... | A61F 5/003 606/139 |
| 2009/0171218 A1 | 7/2009 | Nygaard et al. | | |
| 2010/0222744 A1 | 9/2010 | Riek et al. | | |
| 2011/0288563 A1 | 11/2011 | Gianotti et al. | | |
| 2012/0053485 A1* | 3/2012 | Bloom | ............... | A61B 1/00087 600/567 |
| 2015/0245848 A1 | 9/2015 | Shimon | | |
| 2015/0359524 A1* | 12/2015 | Lubock | ............... | A61B 10/0275 600/567 |
| 2016/0367231 A1 | 12/2016 | Uemichi et al. | | |
| 2017/0086802 A1 | 3/2017 | Mamiya et al. | | |

FOREIGN PATENT DOCUMENTS

| | | | |
|---|---|---|---|
| CN | 204336970 | | 5/2015 |
| CN | 106725249 | | 5/2017 |
| CN | 106725249 A | * | 5/2017 |
| CN | 107666864 | | 2/2018 |

* cited by examiner

RAMPED BIOPSY NEEDLE DEVICE

PRIORITY CLAIM

The present disclosure claims priority to U.S. Provisional Patent Application Ser. No. 62/664,674 filed Apr. 30, 2018; the disclosure of which is incorporated herewith by reference

FIELD

The present disclosure relates to biopsy devices, and more specifically, to biopsy devices for use in bronchospoic and endoscopic procedures.

BACKGROUND

Tissue samples are often examined to determine the presence of a pathological disorder within lung peripheries. If tissue masses or nodules of less than a certain size are identified, a patient may get a biopsy to determine if the mass is benign or malignant. Nodules within the lungs may be concentric or eccentric. Concentric nodules completely surround the perimeter of an airway while eccentric nodules touch only a percentage of the perimeter of the airway and are primarily adjacent to an airway. Current methods for acquiring tissue in the lung periphery have often produced less than adequate yields, especially for eccentric nodules. Furthermore, current systems require multiple device insertions to sample tissue eccentric to the initial needle placement. However, because such biopsies are often done "blindly" distally beyond the vision capabilities of a bronchoscope through which the needle is inserted, pulmonologists are generally unable to identify the site of an initial needle placement, and so often perform multiple passes of the biopsy needle all at the same randomly select needle location.

SUMMARY

The present disclosure is directed to a biopsy needle system including a needle extending from a tissue piercing distal end to a proximal end, the needle defining a lumen extending from the distal end at least a portion of a length thereof and configured to house a target tissue, an elongated member extending from a proximal end to a distal end, the elongated member defining a channel therethrough open at the proximal end, the channel sized and shaped to permit passage of the needle therethrough and an end cap coupled to the distal end of the elongate member, the end cap including a hole extending through a lateral wall thereof, the hole being sized and shaped to permit passage of the needle therethrough, the end cap further comprising a ramp extending from the channel of the elongated member to the hole to guide the needle through the hole, the ramp being angled with respect to a longitudinal axis of the elongated member.

In an embodiment, the elongated member is braided to promote torque transmission along a length thereof.

In an embodiment, the elongated marker includes a plurality of visual markers spaced at regular intervals about a circumference thereof, the visual markers denoting degrees of rotation.

In an embodiment, the elongated marker includes four visual markers separated about the circumference of the elongated marker by 90 degrees.

In an embodiment, the plurality of markers extend along at least a portion of a length of the elongated member in a direction parallel to the longitudinal axis of the elongated member.

In an embodiment, the ramp is angled between 5 and 25 degrees relative to the longitudinal axis of the elongated member.

In an embodiment, the system includes a collar extending from a proximal end to a distal end, the collar configured to be slidably received over a proximal end of the end cap such that the distal end of the collar extends over a proximal portion of the hole, the collar having a rigidity greater than a rigidity of the needle such that the distal end of the collar forms a first point of contact with the needle to deflect the needle without deflecting the catheter.

In an embodiment, the ramp of the end cap is configured to have second and third points of contact with the needle forming a three-point bend system to deflect the needle without deflecting the catheter.

In an embodiment, the needle includes a distal cutting edge, the distal cutting edge being one of oblique or beveled relative to a longitudinal axis of the needle.

The present disclosure is also directed to a device for guiding a biopsy needle including an elongated member extending from a proximal end to a distal end, the elongated member defining a channel therethrough open at the proximal end, the channel sized and shaped to permit passage of a needle therethrough and an end cap coupled to the distal end of the elongate member, the end cap including a hole extending through a lateral wall thereof, the hole being sized and shaped to permit passage of the needle therethrough, the end cap further comprising a ramp extending from the channel of the elongated member to the hole to guide the needle through the hole, the ramp being angled with respect to a longitudinal axis of the elongated member.

In an embodiment, the elongated member is braided to promote torque transmission along a length thereof.

In an embodiment, the elongated marker includes a plurality of visual markers spaced at regular intervals about a circumference thereof, the visual markers denoting degrees of rotation.

In an embodiment, the elongated marker includes four visual markers separated about the circumference of the elongated marker by 90 degrees.

In an embodiment, the plurality of markers extend along at least a portion of a length of the elongated member in a direction parallel to the longitudinal axis of the elongated member.

In an embodiment, the ramp is angled between 5 and 25 degrees relative to the longitudinal axis of the elongated member.

The present disclosure is also directed to a method for obtaining a biopsy sample including inserting an elongated member to a target area within a living body, the elongated member extending from a proximal end to a distal end, the elongated member defining a channel therethrough open at the proximal end, the channel sized and shaped to permit passage of the needle therethrough, the elongated member also including an end cap coupled to the distal end thereof, the end cap including a hole extending through a lateral wall thereof, the hole being sized and shaped to permit passage of the needle therethrough, the end cap further comprising a ramp extending from the channel of the elongated member to the hole to guide the needle through the hole, the ramp being angled with respect to a longitudinal axis of the elongated member, advancing a needle through the channel of the elongated member until a distal end thereof exits the hole of the end cap, the needle extending from a proximal end to the distal end, the needle defining a lumen extending from the distal end at least a portion of a length thereof and configured to house a target tissue and piercing the target tissue with the distal end of the needle, a portion of the target tissue being retained within the lumen of the needle.

In an embodiment, the method further includes withdrawing the needle proximally from the elongated member, rotating the elongated member about its longitudinal axis a known amount such that the hole of the end cap is adjacent to a second portion of the target tissue different from the first portion and reinserting the needle through the channel of the elongated member until a distal end thereof exits the hole of the end cap so that the needle pierces the second portion of target tissue.

In an embodiment, the elongated marker includes a plurality of visual markers spaced at regular intervals about a circumference thereof, the visual markers denoting degrees of rotation.

In an embodiment, the plurality of markers extend along at least a portion of a length of the elongated member in a direction parallel to the longitudinal axis of the elongated member.

In an embodiment, the method further includes acquiring a CT scan of the target area to determine a map a path within in the body from an insertion point to the target tissue.

BRIEF DESCRIPTION

DETAILED DESCRIPTION

Figure 1:
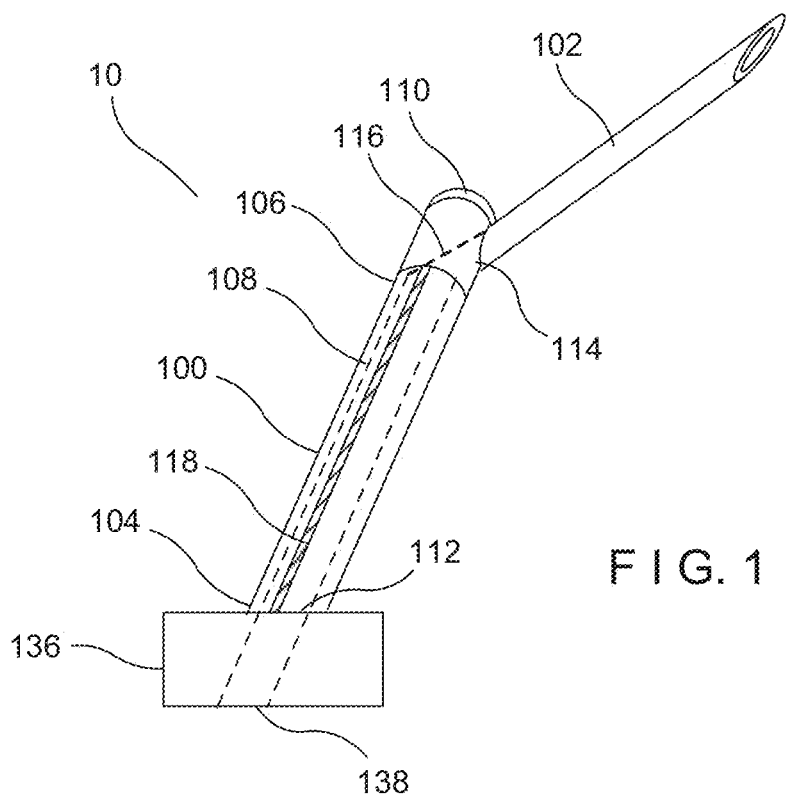
FIG. 1 shows a perspective, partially transparent view of a biopsy device system according to an exemplary embodiment of the present disclosure.

The present disclosure may be further understood with reference to the following description and the appended drawings, wherein like elements are referred to with the same reference numerals. The present disclosure relates to a biopsy device for obtaining tissue samples. Specifically, the present disclosure relates to a needle biopsy device that provides control over needle orientation during use of the device. Exemplary embodiments of the present disclosure describe a catheter with a distal needle ramp. It should be noted that the terms "proximal" and "distal," as used herein, are intended to refer to toward (proximal) and away from (distal) a user of the device.

A biopsy device 10, according to exemplary embodiments of the present disclosure, is depicted in FIG. 1. The biopsy device 10 comprises a catheter 100 inserted into the body via the working channel of an endoscope, bronchoscope or other access device (e.g., inserted into the body along a tortuous path via a natural body lumen accessed via a naturally occurring body orifice) and a biopsy needle 102 slidably received in the catheter 100. The catheter 100 comprises an elongated member extending longitudinally from a proximal end 104 to a distal end 106 and including a lumen 108 extending therethrough and has a length selected to enable the distal end of the catheter 100 and the needle 102 to reach a target site within the body which may be inaccessible to the insertion device and so beyond any vision capabilities of the insertion device. The catheter 100 according to this embodiment is substantially tubular and, as would be understood by those skilled in the art, is made of a suitable biocompatible material such as polyurethane, plastic, or any other such material. Other suitable cross-sectional shapes such as elliptical, oval, polygonal, or irregular may also be contemplated. As would be understood by those skilled in the art, the catheter 100 according to this embodiment is flexible along its entire length or adapted for flexure along selected portions of its length as required to reach the target tissue. It will be understood that the stiffness of the catheter 100 may be modified for use in various lumen diameters and various locations within the body. An end cap 110 is disposed at the distal end 106 of the catheter 100. The catheter 100 includes an opening 112 at the proximal end 104 (or at any other location in a proximal portion of the catheter 100 suitable for accessing the needle 102 and moving the needle 102 relative to the catheter 100 as desired) open to the lumen 108 and is sized and shaped to slidably receive the biopsy needle 102 therein. In this exemplary embodiment, the catheter 100 is braided to promote torque transmission along its length so that rotation applied to the proximal end of the catheter 100 results in a desired rotation of the distal end of the catheter 100. In other exemplary embodiments, the catheter 100 may be coiled or may be a hypotube as would be under stood by those skilled in the art.

In this exemplary embodiment, the catheter 100 includes a plurality of visual markers 118 spaced about a circumference thereof to provide a visual indication of the rotational orientation of the catheter 100. For example, the catheter 100 may include stripes or lines extending longitudinally from the proximal end 104 to the distal end 106. The markers 118 may be different colors or patterns and are separated by, for example, 90 degrees about the circumference of the catheter 100. Alternatively, these lines may be positioned only on a proximal portion of the catheter 100 so that, through observation of the rotation of the proximal portion of the catheter 100, rotation of the distal end of the catheter 100 may be inferred. In this embodiment, the catheter 100 includes four visual markers 118 to aid in achieving a desired rotation of the biopsy needle 102. However, it will be understood that any number of markers 118 may be used so long as they are positioned at regular known intervals about the circumference of the catheter 100 to indicate to the user specific a rotational orientation of the distal end of the catheter 100. It will be understood that the markers 118 do not need to extend the entire length of the catheter 100, but may be positioned at the proximal end 104 and the distal end 160, so long as they are visible to the user of the device 100.

The end cap 110 may be integrally formed with the catheter 100 or it may be a separate component coupled or clipped on to the catheter 100, as shown in FIG. 1. The end cap 110 may be coupled to the catheter 100 via any suitable means such as, for example, welding, interference fit, adhesive, etc. The end cap 110 defines a ramped lateral opening 114 open to the lumen 108 of the catheter 100 and sized and shaped to allow the passage of the biopsy needle 102 therethrough from the lumen 108. This ramped lateral opening 114 directs the biopsy needle 102 away from a longitudinal axis of the catheter 100 at an angle toward the airway wall rather than projecting it out coaxially with the longitudinal axis of the catheter 100 facilitating the positioning of the needle 102 relative to the targeted tissue and allowing the needle 102 to enter different portions of a lesion separated from one another about the circumference of the airway as the catheter 100 and the opening 114 are rotated within the airway. A ramp 116 positioned within the end cap 110 leading from the lumen 108 to the lateral opening 114 is inclined at an angle relative to the longitudinal axis of the catheter 100 toward the lateral opening 114 such that, as the needle 102 is moved distally through the lumen 108, the ramp 114 deflects the needle 102 and directs it through the lateral opening 114 of the end cap 110 angled relative to the longitudinal axis of the catheter 100 which, as the catheter 100 is received within the airway, is generally parallel to the longitudinal axis of the airway. Thus, the ramp 116 provides for a controlled exit of the biopsy needle 102 from the catheter 100 at an angle relative to the longitudinal axis of the airway to enter a portion of a lesion circumferential to all or a part of the airway at a location that can be changed by rotating the catheter 100 within the airway. In this way, rotation of the catheter 100 permits a user to insert the needle 102 into portions of target tissue separated from one another circumferentially about the airway by simply rotating the catheter 100 within the airway. In this exemplary embodiment, the ramp 116 is angled approximately 5-25 degrees relative to the longitudinal axis, L of the catheter 100. However, it will be understood by those skilled in the art that the slope of the ramp may be any desired angle, depending on the procedure and the anatomy to be accessed.

The lateral opening 114 provides the user with improved control over the location from which tissue sample locations are taken after an initial sampling. For example, after an initial tissue sampling, the catheter 100 may be rotated prior to each subsequent sampling so that the lateral opening 114 is directed toward a different area around the circumference of the airway so that the needle 102 can be sequentially directed into each of these different areas. This permits multiple biopsies of different portions of tissue to be taken without removal of the catheter 100 from the airway. Furthermore, the angulation of the needle toward the airway wall allows for enhanced eccentric lesion tissue sampling. In contrast, current biopsy needles generally allow only for the collection of tissue samples that can be accessed by passing the needle along the longitudinal axis of the device so that the needle passes into tissue at a location determined by the geometry of the airway and is not easily controllable by a user. If, for example, a device is positioned adjacent to a bend in the airway, these prior devices could sample tissue only at a location toward which the device is pointed by the geometry of the airway. As would be understood by those skilled in the art, if this location does not correspond to the location of an eccentric lesion, it may be difficult or impossible to obtain a sample with a conventional device.

Figure 2:
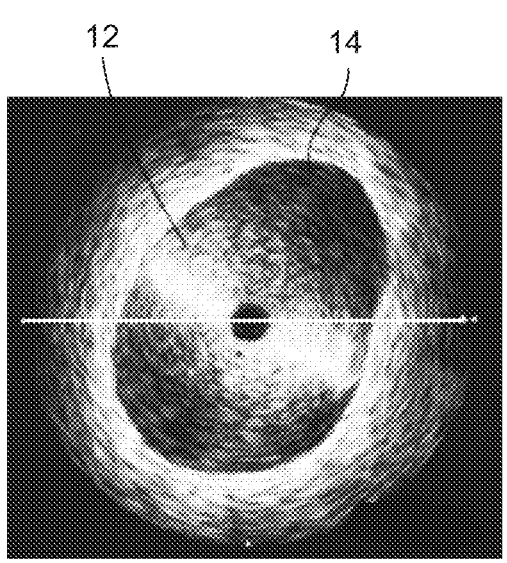
FIG. 2 shows an endobronchial ultrasound image of a concentric lesion.
Figure 3:
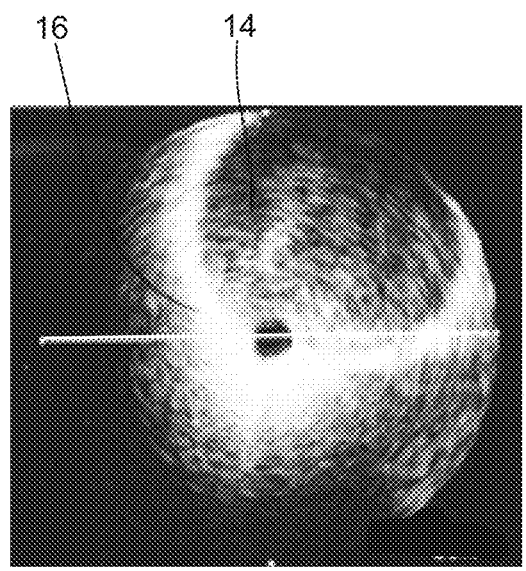
FIG. 3 shows an endobronchial ultrasound image of an eccentric lesion.

As can be seen in FIG. 2, a concentric lesion 12 or nodule completely surrounds the perimeter of the airway. In these cases, a conventional coaxial needle is generally capable of taking a biopsy of the lesion. That is, a needle passing along any axis non-parallel to the axis of the airway at the position of the lesion will always pass through the lesion. Thus, a user may insert the needle to a location in the airway in a bend of the lesion immediately proximal to the portion of the airway surrounded by the lesion. As the axis of the airway at this bed is non-parallel to the axis of the airway at the lesion, the user should always be able to penetrate a fully circumferential or concentric lesion. However, if a lesion does not extend around the full circumference of the airway, this angled axis may not pass through the lesion. Thus, certain eccentric lesions may not be reachable by conventional needles. A biopsy of an eccentric lesion 16, as depicted in FIG. 3, extending around only a portion of the perimeter of the airway 14 may be very difficult to obtain using coaxial needles, resulting in a yield drop of approximately 40%. The current device 10 directs the needle 102 radially away from the longitudinal axis L of the catheter 100 toward the wall of the airway 14 to allow for eccentric sampling by simply rotating the needle 100 to aim the ramp 116 and the lateral opening 114 to different orientations relative to the airway. Furthermore, the user is capable of rotating the device 10 a specific, known amount, using the markers 118, for subsequent biopsies while leaving the catheter 100 within the airway 14. By allowing control over the relative needle exit positions between biopsies, the device 10 provides the user with the ability to acquire more tissue from various locations (around the circumference of the airway) from the same longitudinal position within the airway, increasing confidence and ability to diagnose concentric and eccentric nodules.

Figure 4:
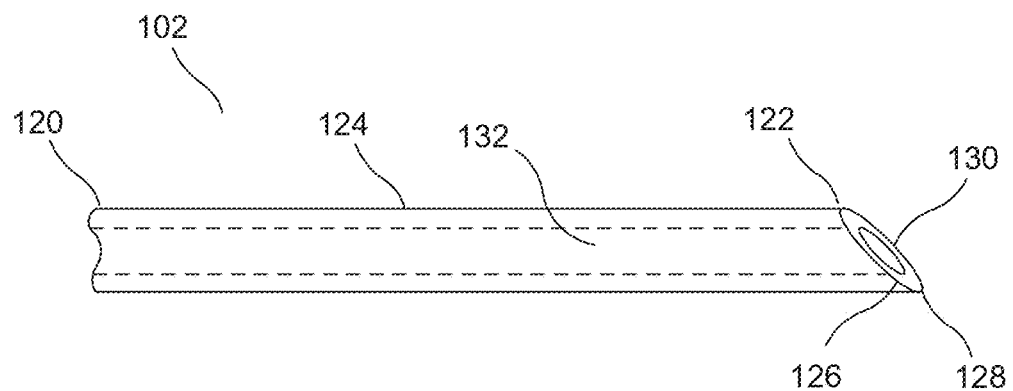
FIG. 4 shows a needle of the biopsy device system of FIG. 1 according to an exemplary embodiment of the present disclosure.
Figure 5:
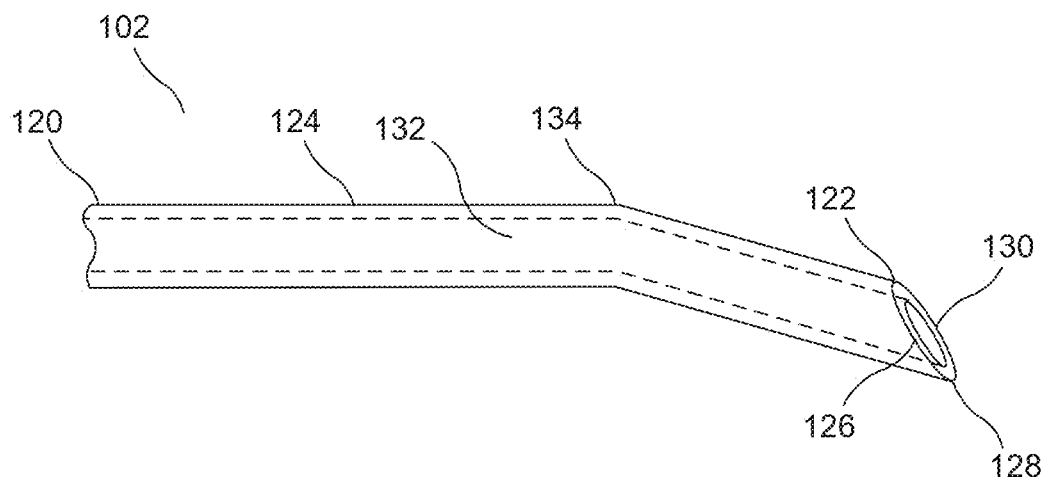
FIG. 5 shows a needle of the biopsy device system of FIG. 1 according to a second exemplary embodiment of the present disclosure.

The biopsy needle 102 extends from a proximal end 120 to a distal end 122 and is sized and shaped to be inserted through the lumen 108 of the catheter 100. This biopsy needle 102, in this embodiment, is preferably constructed of metal or other suitable material and includes an elongate substantially cylindrical body 124 which, in an exemplary embodiment, terminates in a tapered distal end portion 126. In another exemplary embodiment, an outer diameter of the needle 102 is substantially uniform along its length. The distal end 122 includes a tissue-piercing distal tip 128 configured to be inserted into, and pierce, tissue to obtain a biopsy sample. The distal end 122 of this embodiment includes a distal cutting edge 130 which may be oblique or beveled relative to the longitudinal axis of the needle 102 with an opening at the distal end of the needle 102 to permit the entry of penetrated tissue into the lumen 132. In an exemplary embodiment, the needle 102 is flexible along its length (or at least at a distal portion thereof) to allow deflection thereof by the ramp 116 through the opening 114. As can be seen in FIG. 4, at least a distal portion, including the distal end 122, of the biopsy needle 102 is hollow and open at a distal end 122 of the needle 102 to collect and retain target tissue. However, in some embodiments, the needle 102 may include a lumen 132 extending therethrough from the proximal end 120 to the distal end 122. The lumen 132 is open at the distal end 122 so that target tissue penetrated by the needle 102 can be received into the distal end 122 of the needle 102. The lumen 132 may also be open at the proximal end 120. The proximal end 120 may, in an exemplary embodiment, be configured to be coupled to a suction mechanism or device for retrieval of target tissue through the lumen 132 and out of the proximal end 120. In this embodiment, collected tissue may be suctioned through the lumen 132 of the needle 102 from the distal end 122 to the proximal end 120 and, in some instances, into a suction device. In this embodiment, the needle 102 includes a handle or gripping portion at the proximal end 120.

In an exemplary embodiment, the biopsy needle 102 may include a bend 134 adjacent to the distal end 122 for easier passage through the ramped lateral hole 114 and greater angulation toward the target tissue. In an exemplary embodiment, the angle of the bend 134 in the needle 102 may be equal to the angle of the ramp relative to the longitudinal axis of the device 10—i.e., 5 to 25 degrees. In another exemplary embodiment, the angle of the bend 134 may be greater or lesser than the ramp angulation. Because the biopsy needle 102 is formed of a flexible material, during insertion and passage through the lumen 108 of the catheter, the needle 102 is constrained by the walls of the lumen 108 away from its bent configuration to a substantially straight configuration until a portion of the needle distal of the bend 134 passes onto the ramp 116 and then through the opening 114, at which point the needle 102 reverts to its bent configuration under its own natural bias. In an embodiment, the needle 102 may be formed of a shape-memory material such as, for example, Nitinol permitting the needle 102 to return to the bent configuration toward which it is biased after having been constrained to follow the axis of the catheter 100.

The proximal end 104 of the catheter 100 may include a hub or handle 136 attached thereto to be held by the user during insertion and positioning of the device 10. In an exemplary embodiment, the handle 136 may be used for connecting other treatment devices or providing a port for facilitating other treatments. A lumen 138 extends through the handle and is sized and shaped for passage of the biopsy needle 102 therethrough. The catheter 100, in an exemplary embodiment, may be rotated within the airway by rotating the handle 136 a desired amount. However, in some instances, the handle 136 may include an actuator for manipulation of the catheter 100. For example, the handle may include an actuation mechanism for rotation of the catheter 100 in specific, known intervals.

The materials that can be used for the various components of the biopsy devices, systems, or components thereof, such as devices 10, 100, 102 (and/or other structures disclosed herein) and the various members disclosed herein may include those commonly associated with medical devices. For example, the devices 10/100/102 and/or other components of the biopsy system may be made from a metal, metal alloy, polymer, a metal-polymer composite, ceramics, combinations thereof, and the like, or other suitable material. For simplicity purposes, this discussion makes reference to devices 10/100/102 and components thereof. However, this is not intended to limit the devices and methods described herein.

Figure 6:
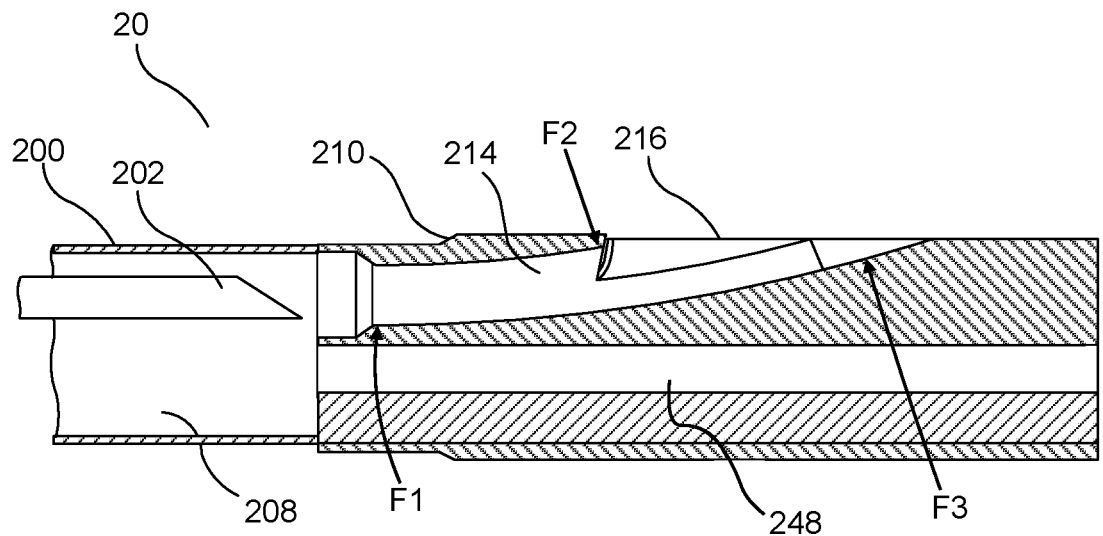
FIG. 6 shows a cross-sectional view of a biopsy device according to another exemplary embodiment of the present disclosure.
Figure 7:
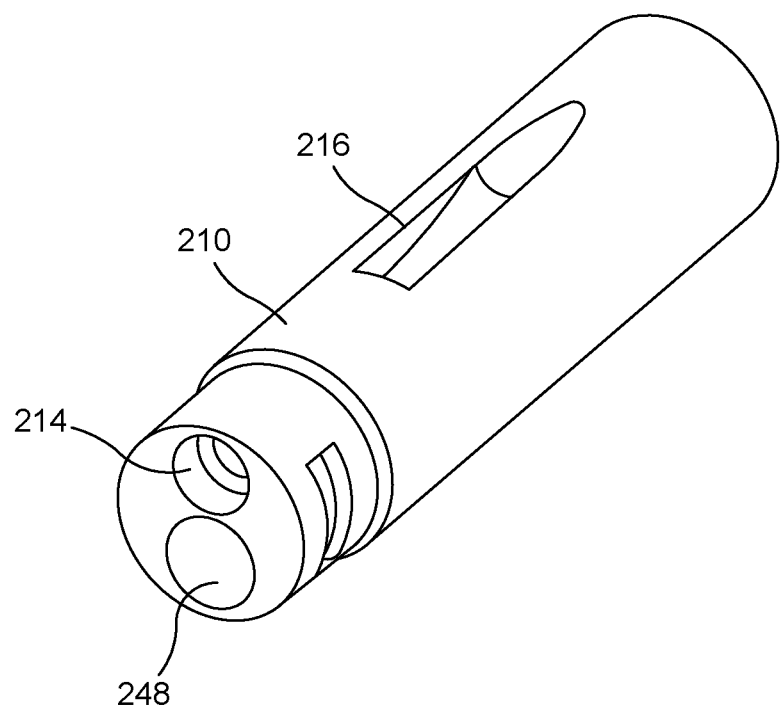
FIG. 7 shows a perspective view of the biopsy device of FIG. 6.

A biopsy device 20, according to another exemplary embodiment of the present disclosure, is depicted in FIGS. 6-7. The biopsy device 20 includes a catheter 200, a biopsy needle 202 and an end cap 210 and is substantially similar to biopsy device 10 except as described herein. The end cap 210 similar to end cap 110, may be integrally formed with the catheter 200 or it may be a separate component coupled or clipped on to the catheter 200. The end cap 210 defines an internal channel 214 open to the lumen 208 of the catheter 200 at a proximal end and a lateral opening 216 at a distal end. The end cap 210 is sized and shaped to allow the passage of the biopsy needle 202 (or other elongate member) therethrough from the lumen 208. The end cap 210, in this embodiment, is a rigid end cap made of a high durometer polymer or metal material such as, for example, polycarbonate, glass filled polymer such as PEEL, Nylon, ABS, etc. Thus, the end cap 210 has a rigidity higher than that of the biopsy needle 202 being passed therethrough. In this embodiment, the internal channel 214 is an arced channel such that the internal channel has three contact points with the biopsy needle 202 being passed therethrough. As depicted in FIG. 6, the three points of contact F1, F2, F3 are positioned along the arc of the internal channel to provide three force loads as found in a three-point bend flexural system, as one skilled in the art would understand. Having all three force loads contained within the rigid end cap 210 ensures that the distal portion biopsy needle 202 being passed through the channel deflects without translating any forces to the proximal portion of the biopsy needle 202 or the catheter 200. Thus, all of the bending load is applied to the biopsy needle 202 within the end cap 210 ensuring that the biopsy needle 202 is the deflected element, not the catheter 200 or end cap 210. As noted above, this rigid end cap 210 is beneficial in procedures which require a catheter that is more flexible than the biopsy needle used. In such a procedure, the needle is often too stiff to be deflected by a simple ramped end cap, causing deflection of the catheter instead and leading to a needle exit angle that is much lower than the desired angle, if any angle can be achieved at all. The end cap 210 with the curved internal channel allows a physician to deflect the needle at the required angle even when the needle has a greater rigidity than the catheter through which it is passed.

Figure 8:
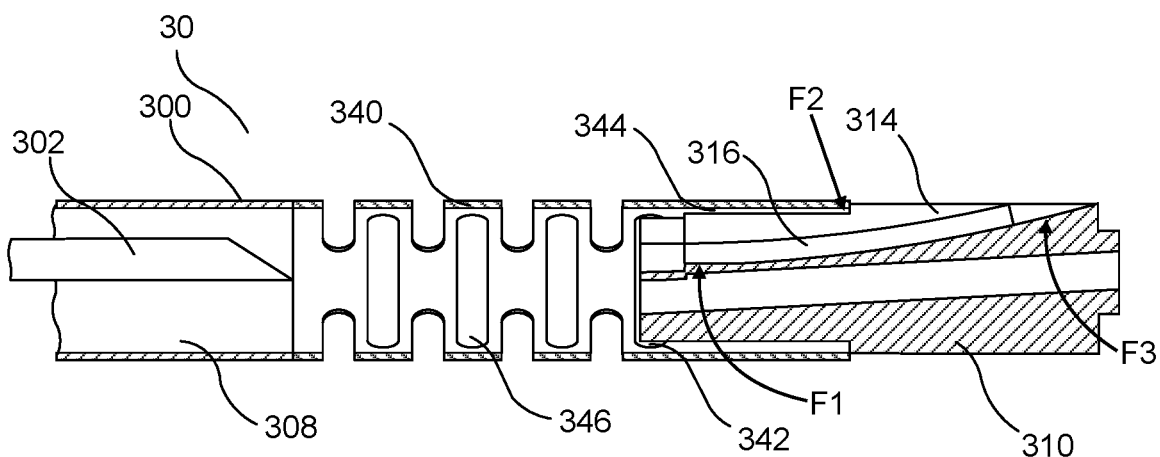
FIG. 8 shows a cross-sectional view of a biopsy device according to a third exemplary embodiment of the present disclosure.
Figure 9:
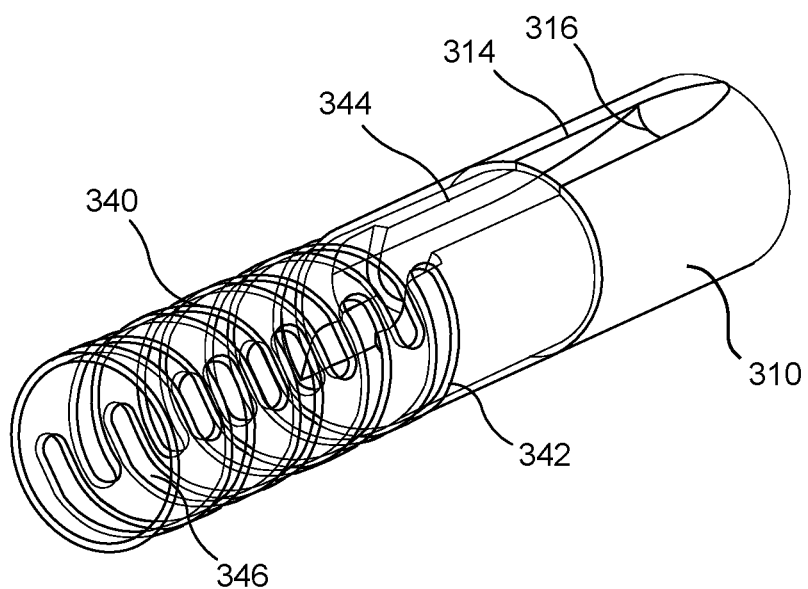
FIG. 9 shows a partially transparent perspective view of the biopsy device of FIG. 8.

A biopsy device 30, according to another exemplary embodiment of the present disclosure, is depicted in FIG. 8-9. The biopsy device 210 includes a catheter 300, a biopsy needle 302 and an end cap 310 and is substantially similar to biopsy devices 10, 20 except as described herein. The end cap 310, similar to end caps 110, 210 may be integrally formed with the catheter 300 or it may be a separate component that is coupled or clipped on to the catheter 300. Similar to device 10, the end cap 310 defines a ramped lateral opening 314 open to a lumen 308 of the catheter 300 and sized and shaped to allow the passage of the biopsy needle 302 therethrough from the lumen 308. Specifically, a ramp 316 is positioned within the end cap 310 leading from the lumen 308 to the lateral opening 314. The ramp 316 is inclined toward the lateral opening 314 such that, as the needle 302 is moved distally through the lumen 308, the ramp 314 directs the needle 302 toward the lateral opening 314 of the end cap 310. It will be understood that the ramp 316 may extend along a straight or curved path toward the lateral opening 314. The end cap 310, in this embodiment, is a rigid end cap made of a high durometer polymer or metal material such as, for example, polycarbonate, glass filled polymer such as PEEL, Nylon, ABS, etc. Thus, the end cap 310 has a rigidity higher than that of the biopsy needle 302 being passed therethrough. As with device 20, the device 30 deflects the biopsy needle 302 via three points of contact F1, F2, F3. However, in this embodiment, points of contact F1, F3 are formed by the ramp 316 while point of contact F2 is formed by a deflection collar 340. The tubular deflection collar 340 of this embodiment is sized and shaped to be positioned over a proximal end 342 of the end cap 310 such that a distal portion 344 of the collar 340 extends over a proximal portion of the lateral opening 314, creating a contact point F2 for deflection of the biopsy needle 302. The collar 340 may be positioned over the end cap 310 in any known manner. For example, the collar 340 may be slidably positioned over the proximal end of the end cap 310 and held in place via a friction fit, interference fit, etc. A proximal end of the collar 340 is coupled to a distal end of the catheter 300 in any known manner such as, for example, friction fit, interference fit, etc. In this embodiment, the lateral opening 314 may be elongated (i.e., in a direction parallel to the longitudinal axis of the device 30), as shown in FIG. 9, such that positioning of the collar 340 (i.e., more distally, more proximally) determines the degree to which the biopsy needle 302 is deflected. The collar 340 is a rigid collar made of a high durometer polymer or metal material such as, for example, polycarbonate, glass filled polymer such as PEEL, Nylon, ABS, etc. This rigidity of the collar 340 provides enough force load, along with points of contact F1 and F3 along the ramp 316 to deflect the biopsy needle 302 while preventing translation of the deflection force to the catheter 300 instead. However, as can be seen in FIGS. 8-9, a proximal portion of the collar 340 may be formed with a plurality of slots or cutouts 346. These slots 346 increase the flexibility of the proximal portion of the collar to allow the device 30 to more easily navigate through tortuous anatomy and reach the target site. As with biopsy device 20, the end cap 310, in combination with the collar 340, provides the force load necessary to bend a biopsy needle in procedures where the biopsy needle has a greater rigidity than the delivery catheter.

Although the biopsy devices 10, 20, 30 are described as only including a single channel or opening through the end caps 110, 210, 310, it will be understood by those skilled in the art that the end caps may also include a second channel extending along the longitudinal axis of the biopsy device or parallel thereto. This allows the user to have the option of actuating the needle in a straight configuration or a bent configuration. As an example, FIGS. 6-7 depict biopsy device 20 as including a second channel 248 extending substantially parallel to the longitudinal axis of the device 20.

In an exemplary method according to the present disclosure, the biopsy needle device 10 may be used in combination with Super Dimension technology. It is understood that although reference is made to biopsy needle device 10, the present method may be performed with any of the disclosed devices 10, 20, 30. In this method, a CT scan of, in this case, the lung is acquired before the procedure to determine and map an appropriate path to the nodule/lesion. During the procedure, the map is used to direct a bronchoscope to a location as near the biopsy site as possible using standard procedures. With the bronchoscope in place, the distal end 106 of the catheter 100 is inserted and advanced distally therethrough out of a distal end of the bronchoscope to a target biopsy site within the body (e.g., within an airway of the lung). Once the catheter 100 has been positioned within the airway as desired (e.g., using an external vision system when the distal end of the catheter is no longer visible using the vision system of the bronchoscope), the needle 102 is advanced through the lumen 108 of the catheter 100 until the distal end thereof is deflected by the ramp 116 and exits the lateral opening 114 at an angle relative to the catheter 100. The needle 102 is further distally advanced into a first biopsy site within a lesion to collect a biopsy sample. After the sample has been obtained, the needle 102 may be withdrawn proximally through the lumen 108 and sample may be removed and preliminarily examined to determine if it is sufficient. If more sample tissue is needed, the catheter 100, which has been maintained at the same location within the airway, is rotated a desired amount using the visual markers 118, in this embodiment 90 degrees, and the biopsy needle 102 is re-inserted through the lumen 108, out the opening 114, and into a second biopsy site within the same lesion to collect a second biopsy sample. After the sample has been obtained, the needle 102 may be withdrawn proximally through the lumen 108 and the second sample may be reviewed to determine if more tissue is required. Those skilled in the art will understand that, alternatively, the tissue samples may be suctioned through a lumen such as the lumen 132 of needle 102 and reviewed without removing the needle 102 from the body. If more tissue is required, the method continues until the biopsy needle 102 has sampled tissue from various locations around the circumference of the airway. The needle 102 and catheter 100 are then retracted from the bronchoscope and removed from the body.

A second exemplary method according to the present disclosure, uses Olympus radial endobronchial ultrasound (ESUS) technology. Initially, a guide sheath with an ultrasound probe positioned in a channel thereof is inserted (e.g., through a body lumen) into the lung. The guide sheath, with the ultrasound probe therein, is capable of being advanced into the lung further than a typical bronchoscope and is used to locate the target nodule. Once the guide sheath has been positioned within the airway near the target nodule as desired, the ultrasound probe is removed from the guide sheath and the catheter 100 is advanced through the lumen of the guide sheath until the distal end 106 is positioned adjacent the target nodule. With the catheter 100 in place, the method proceeds as described above. Specifically, the needle 102 is advanced through the lumen 108 of the catheter 100 until the distal end thereof is deflected by the ramp 116 and exits the lateral opening 114 at an angle relative to the catheter 100. The needle 102 is further distally advanced into a first biopsy site to collect a biopsy sample. After the sample has been obtained, the tissue sample is observed to determine if additional samples are required. If more sample tissue is required, the catheter 100 is rotated a desired amount using the visual markers and the biopsy needle 102 is re-inserted through the lumen 108, out the opening 114, and into a second biopsy site to collect a second biopsy sample and the method continues until the biopsy needle 102 has obtained adequate sample tissue from various locations around the circumference of the airway. The needle 102 and catheter 100 are then retracted from the bronchoscope and the guide sheath and removed from the body. It is understood that although reference is made to biopsy needle device 10, the present method may be performed with any of the disclosed devices 10, 20, 30.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiments disclosed, but rather modifications are also covered within the scope of the present invention as defined by the appended claims.

What is claimed is:

1. A device for guiding a biopsy needle, comprising:
    an elongated member extending from a proximal end to a distal end, the elongated member defining a channel therethrough open at the proximal end, the channel sized and shaped to permit passage of the biopsy needle therethrough;
    an end cap coupled to the distal end of the elongate member, the end cap including a hole extending through a lateral wall thereof, the hole being sized and shaped to permit passage of the needle therethrough, the end cap further comprising an arced surface forming a ramp extending from the channel of the elongated member to the hole to guide the needle through the hole, the arced surface of the channel including two points of contact positioned along the ramp of the channel configured to provide force loads to the needle through the hole without translating forces to the proximal end of the elongated member; and a deflection collar sized and shaped to be positioned over a proximal end of the end cap such that a distal portion of the collar extends over a proximal portion of the hole, creating a third contact point for deflection of the needle.

2. The device of claim 1, wherein the elongated member is braided to promote torque transmission along a length thereof.

3. The device of claim 1, wherein the elongated member includes a plurality of visual markers spaced at regular intervals about a circumference thereof, the visual markers denoting degrees of rotation.

4. The device of claim 3, wherein the elongated member includes four visual markers separated about the circumference of the elongated member by 90 degrees.

5. The device of claim 3, wherein the plurality of markers extends along at least a portion of a length of the elongated member in a direction parallel to a longitudinal axis of the elongated member.

6. The device of claim 1, wherein the ramp is angled between 5 and 25 degrees relative to a longitudinal axis of the elongated member.

7. The device of claim 1, wherein the deflection collar is slidably positioned over the end cap and held in place via a friction or interference fit.

8. The device of claim 1, wherein the hole is elongated in a direction parallel to a longitudinal axis of the device such that the positioning of the deflection collar determines a degree to which the biopsy needle is deflected.

9. The device of claim 1, wherein the deflection collar is formed with a plurality of slots or cutouts to increase a flexibility of the proximal portion of the collar and allow the device to more easily navigate through tortuous anatomy and reach a target site.

* * * * *